(12) United States Patent
Brockett

(10) Patent No.: US 8,444,719 B2
(45) Date of Patent: May 21, 2013

(54) METHOD AND APPARATUS FOR THE BATCH PREPARATION OF BIODIESEL

(75) Inventor: Gary Brockett, Auckland (NZ)

(73) Assignee: Ecodiesel Limited, Auckland (NZ)

( * ) Notice: Subject to any disclaimer, the term of this patent is extended or adjusted under 35 U.S.C. 154(b) by 444 days.

(21) Appl. No.: 12/669,460

(22) PCT Filed: Jul. 16, 2008

(86) PCT No.: PCT/NZ2008/000178
§ 371 (c)(1),
(2), (4) Date: Jun. 1, 2010

(87) PCT Pub. No.: WO2009/011604
PCT Pub. Date: Jan. 22, 2009

(65) Prior Publication Data
US 2010/0229460 A1    Sep. 16, 2010

(30) Foreign Application Priority Data
Jul. 16, 2007   (NZ) .................................. 556530

(51) Int. Cl.
*C10L 1/18*   (2006.01)
(52) U.S. Cl.
USPC .............. 44/388; 554/161; 554/163; 554/170
(58) Field of Classification Search
USPC .................... 44/308, 388; 554/124, 161, 163, 554/170
See application file for complete search history.

(56) References Cited

U.S. PATENT DOCUMENTS
7,666,234 B2 *   2/2010   Ghosh et al. .................... 44/308

OTHER PUBLICATIONS

First Notification of Examiner's Opinion in Chinese; Title: Method and Apparatus for the Batch Preparation of Biodiesel; Filing No. 200880025126.7; Applicant: Gary Brockett; Issue Date Jan. 30, 2012; 6 Pages.
First Notification of Examiner's Opinion (English translation) PCT Application Entering the Chinese National Phase; Title: Method and Apparatus for the Batch Preparation of Biodiesel; Filing No. 200880025126.7; Applicant: Gary Brockett; Issue Date Jan. 30, 2012; ANSEN Patent Law Office, Beijing, PR China; 9 Pages.
PCT Application No. PCT/NZ2008/000178, Filed Aug. 16, 2008, Brockett, G., International Preliminary Report on Patentability Issued Jan. 19, 2010.
PCT Application No. PCT/NZ2008/000178 Filed Aug. 16, 2008, International Search Report Issued Sep. 18, 2008.
English Translation: First Notification of Examiner's Opinion (9 sheets including cover); Filing No. 20080025126.7; Issue Date: Jan. 30, 2012.

* cited by examiner

*Primary Examiner* — Cephia D Toomer

(57) ABSTRACT

The invention relates to a method and apparatus for the batch preparation of esters of fatty acids obtained from biological sources. In particular, the invention relates to a method and apparatus for the batch preparation of methyl esters of fatty acids obtained from waste oil or animal fats for use as biodiesel.

11 Claims, 1 Drawing Sheet

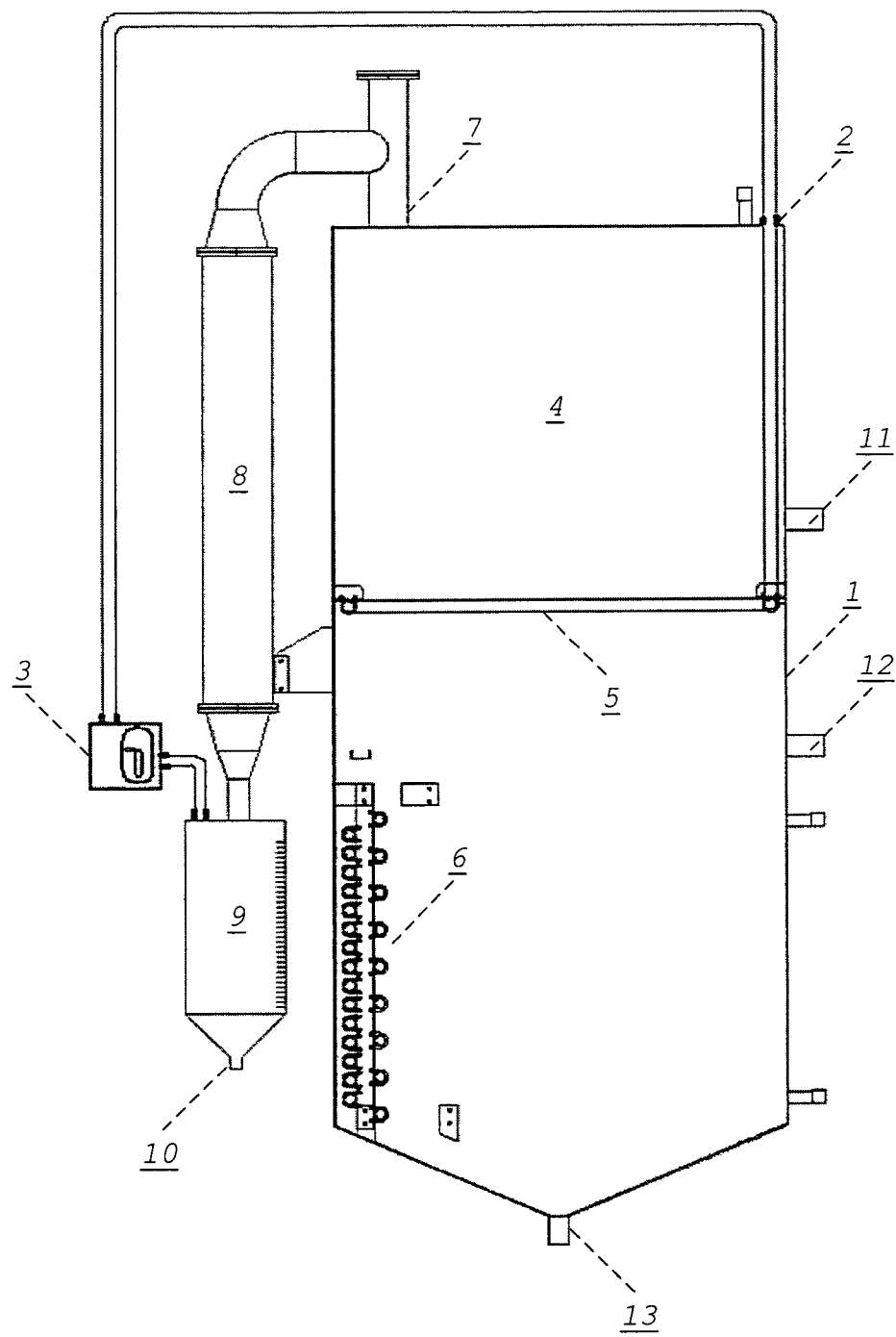

METHOD AND APPARATUS FOR THE BATCH PREPARATION OF BIODIESEL

TECHNICAL FIELD

The invention relates to a method and apparatus for the batch preparation of esters of fatty acids obtained from biological sources.

In particular, the invention relates to a method and apparatus for the batch preparation of methyl esters of fatty acids obtained from waste oil or animal fats for use as biodiesel.

BACKGROUND ART

Biodiesel is produced by transesterification of oils with short-chain alcohols or by the esterification of fatty acids. The transesterification reaction consists of transforming triglycerides into fatty acid alkyl esters in the presence of a short chain alcohol, such as methanol or ethanol, and a catalyst, such as an alkali, with glycerol as a by-product.

Biodiesel as a fuel is attracting increasing attention worldwide as a direct replacement for diesel in vehicle engines or, more commonly, as a blending component for diesel (Judd, 2002). The majority of biodiesel today is produced by alkali-catalyzed transesterification of oil or fat with methanol, in the presence of an alkali catalyst which results in a relatively short reaction time (Vasudevan and Briggs, 2008).

Waste vegetable oils and animal fats (tallow) are sources of oil or fat that may be used in the preparation of biodiesel.

Sims (1983) noted the availability of substantial quantities of tallow in New Zealand as an opportunity for local biodiesel production.

In 2002, some 150,000 tonnes per annum of tallow was produced in New Zealand and some 2 million tonnes per annum of diesel was used (Judd, 2002). At these production and use rates a 6% biodiesel/mineral diesel blend could be produced satisfying local demand using locally sourced tallow.

Where the demands for biodiesel production are higher, biodiesel is most commonly prepared by a continuous, as opposed to batch, reaction process. Plant capacities in excess of 100,000 tonnes per annum are known.

Economic justification for the commissioning and operation of Plant with these capacities does not exist while the local demand for biodiesel production is relatively low. Economic justification for the commissioning and operation of plant with these capabilities does not exist when the sources of oil or fat are distributed across remote areas.

The preparation of biodiesel by a batch reaction process may be appropriate while the local demand for biodiesel production is relatively low or the sources of oil or fat are distributed across remote areas. In these circumstances plant that is cost effective to establish and operate is required.

The preparation of biodiesel from waste oil or animal fats (tallow) requires pre-treatment of the source of oil or fat to remove excess entrained water and/or free fatty acids that would otherwise interact with the alkali catalyst to form soaps.

It is an object of the invention to provide a method of preparing biodiesel that is particularly suited for use in batch manufacturing processes using tallow as a source of fat.

It is an object of the invention to provide apparatus adapted for use in preparing biodiesel that is particularly suited for use in batch manufacturing processes using tallow as a source of fat.

These objects are to be read disjunctively with the object of to at least provide a useful choice.

DISCLOSURE OF INVENTION

In a first aspect the invention provides a method of preparing biodiesel from a source of oil or fat by a batch production process including the step of:
  Aerating a volume of the source of oil or fat in a vessel at a temperature and for a time sufficient to provide a dehydrated source of oil or fat and a vapour laden air stream.
Preferably, the method includes the step of:
  Passing the vapour laden air stream through a heat exchanger to condense the vapour and provide a dried air stream.
More preferably, the method includes the step of:
  Aerating the volume of the source of oil or fat with the dried air stream.
Preferably, the source of oil or fat contains greater than 0.5% (w/w) water.
Preferably, the source of oil or fat contains 1 to 4% (w/w) free fatty acids.
Preferably, the source of oil or fat is tallow.
Preferably, the temperature is 60 to 65° C.
In a second aspect the invention provides a method of preparing biodiesel from a dehydrated source of oil or fat including the step of:
  Combining a volume of the dehydrated source of oil or fat with a volume of short chain alcohol in a vessel in the presence of a concentration of mineral acid catalyst at a temperature and for a time sufficient to provide an esterified, dehydrated source of oil or fat with a free fatty acid content reduced to less than (w/w).
In a third aspect the invention provides a method of preparing biodiesel from a dehydrated source of oil or fat including the steps of:
  Combining a volume of the dehydrated source of oil or fat with a volume of short chain alcohol in a vessel in the presence of a concentration of alkali catalyst at a temperature and for a time sufficient to convert greater than 95% of the fatty acids to alkyl esters;
  Aerating the combined volume at a temperature and for a time sufficient to provide an alcohol laden air stream; and
  Passing the alcohol laden airstream through a heat exchanger to condense the alcohol and provide a dealcoholised airstream.
Preferably, the method includes the step of:
  Aerating the combined volume with the dealcoholised airstream.
Preferably, the temperature and the time are sufficient to convert greater than 99% of the fatty acids to alkyl esters.
Preferably, the source of oil or fat is tallow.
Preferably, the ratio of the volume of the source of oil or fat to the volume of alcohol is less than 1.
Preferably, the temperature is 60 to 65° C.
Preferably, the alcohol is methanol.
Preferably, the time is less than 2 hours.
Preferably, the vessels of the first, second and third aspects of the invention are the same.
A preferred embodiment combining the first, second and third aspects of the invention provides a method of preparing a biodiesel from tallow by a batch production process including the steps of:
  Aerating a volume of tallow in a vessel at a temperature of 60 to 65° C. to provide a vapour laden air stream;

Passing the vapour laden air stream through a heat exchanger to condense the vapour and provide a dried air stream;

Aerating the volume of tallow in the vessel with the dried air stream at the temperature of 60 to 65° C. for a time sufficient to provide a volume of dehydrated tallow;

Optionally combining the volume of dehydrated tallow with a volume of methanol in the vessel in the presence of a concentration of mineral acid catalyst at the temperature of 60 to 65° C. for a time sufficient to provide a volume of dehydrated tallow with a free fatty acid content reduced to less than 1.5% (w/w);

Combining the volume of dehydrated tallow with a volume of methanol in the vessel in the presence of a concentration of alkali catalyst at the temperature of 60 to 65° C. for a time sufficient to provide a combined volume where greater than 99% of the fatty acids are converted to alkyl esters;

Aerating the combined volume in the vessel at the temperature of 60 to 65° C. to provide a methanol laden air stream;

Passing the methanol laden-airstream through a heat exchanger to condense the methanol and provide a dealcoholised airstream; and Aerating the combined volume in the vessel with the dealcoholised airstream at the temperature of 60 to 65° C. for a time sufficient to provide the biodiesel.

Preferably, the source of oil or fat contains greater than 0.5% (w/w) water.

Preferably, the source of oil or fat contains 1 to 4% (w/w) free fatty acids.

Preferably, the combining a volume of the dehydrated tallow with a volume of methanol in the vessel is at a ratio of less than 1.

Preferably, the method includes the additional step of:

Removing glycerol from the combined volume.

In a fourth aspect the invention provides an apparatus for use in the method of the preferred embodiment including a vessel for receiving a volume of a source of oil or fat to be converted to alkyl esters and a heat exchanger where the vessel is provided with at least one inlet adapted to receive a flow of air from the heat exchanger into the volume and at least one outlet from which the flow of air can be conveyed to the heat exchanger.

In the description and claims of the specification the following terms are intended to have the meanings provided:

"Aeration" means the passage of air through a volume of liquid, and "aerating" has a corresponding meaning.

"Air" means a mixture of mainly nitrogen and includes nitrogen.

"Batch production process" means a production process where the steps of the production process are performed in the same vessel.

"Biodiesel" means the alkyl esters of the fatty acids of vegetable oils and animal fats.

"Dehydrated source of oil or fat" means a source of oil or fat for which the water content has been reduced to less than 0.5% (w/w).

"Fatty acids" means long chain carboxy acid residues in either their esterified (alkyl esters, triglycerides), acid or salt forms.

"Tree fatty acids" means long chain carboxy acid residues in their acid or salt forms (non-esterified).

"Tallow" means the fatty substance made from rendered animal fat.

"Trans-esterification" means the preparation of alkyl esters of fatty acids by mixing fat or oil with a short chain alcohol in the presence of an alkali catalyst, commonly sodium hydroxide or potassium hydroxide, and "trans-esterified" has a corresponding meaning.

An exemplary embodiment of the invention will now be described in detail with reference to the Figures of the accompanying drawings pages.

BRIEF DESCRIPTION OF FIGURES

FIG. 1. Apparatus for the batch production of biodiesel comprising vessel (1), inlet (2), gas recirculator (3), reactor tank (4), air sparge line (5), heating and cooling coils (6), outlet (7), heat exchanger (8), graduated tank (9), outlet valve (10) and additional inlet and outlet valves (11, 12 and 13).

DETAILED DESCRIPTION

As summarized by Judd (2002) fatty acid methyl esters are prepared by stirring oil or fat with methanol in the presence of a catalyst, commonly sodium or potassium hydroxide, in a reaction vessel. The oil or fat and alcohol must be substantially anhydrous and have a low free fatty acid content. In the presence of water or free fatty acid soap formation is promoted.

In the method described here the raw tallow is treated by reacting free fatty acids with methanol in the presence of an acid catalyst. If necessary, the tallow is also treated to remove entrained water. As noted, both free fatty acids and water interfere with the trans-esterification reaction.

The pre-treated tallow is then trans-esterified by reacting with excess methanol in the presence of an alkaline catalyst such as sodium hydroxide (NaOH) or potassium hydroxide (KOH).

Crude glycerol may be separated from the methyl esters by settling or centrifugation before passing the esters through a purification stage to give the final product (Biodiesel). The glycerol may be processed separately to recover methanol for recycling to the reaction vessel and to give pure glycerol as a co-product of biodiesel.

A feature of the present invention is the recovery of methanol and/or removal of entrained water from the volume by aeration. A vessel is provided with an inlet for delivery of air in to the volume and an outlet for conveying the methanol and/or water laden air to a heat exchanger. The methanol and/or water is condensed permitting its reuse in, or removal from, the batch manufacturing process.

The feature permits the preparation of biodiesel by the batch production process without the requirement for heating of the volume in the vessel above a temperature sufficient to both:

(i) maintain the tallow in liquid form; and (ii) convert greater the fatty acids to alkyl esters.

Known methods for the removal of entrained water from raw tallow require heating of the tallow to high temperatures (above 100° C.). The raw tallow may be delivered into a spray chamber under reduced pressure or a scraped surface evaporator. These methods necessitate the cooling of the tallow before mixing with methanol (boiling point 65° C.).

The feature of the present invention is therefore particularly advantageous when it is necessary in the batch production process to recover methanol and/or remove entrained water from a volume of tallow or fatty acid methyl esters.

A general method of preparing biodiesel from tallow is now described.

Tallow Dehydration

The dehydrator vessel is typically maintained at 60 to 65° C. Water is removed from the raw tallow by passing a stream of air through the agitated volume via inlet and outlets of the vessel.

The moisture laden air is passed through a heat exchanger where the temperature is lowered and the water condenses. The air is then re-circulated through the volume of tallow to remove further water.

If the tallow is subject to oxidation, nitrogen may be used. As the gas is recycled the operating costs are minimised. Recycling also reduces the release of odours.

Free Fatty Acid Esterification

If the FREE FATTY ACID content of the raw tallow exceeds 1 to 1.5% (w/w), esterification by reacting with excess methanol (MeOH) in the presence of a mineral acid catalyst is performed. With a free fatty acid content of up to 4% (w/w) the free fatty acid can be sufficiently reduced without the requirement for recovery of methanol.

Trans-Esterification

Pre-treated tallow with a free fatty acid content reduced to approximately 1% (w/w) is reacted with excess methanol in the presence of a an alkali catalyst, usually sodium hydroxide (NaOH) or potassium hydroxide (KOH).

Glycerol is formed as a co-product and can be recovered after a period of settling. The trans-esterification step may be repeated to achieve the required conversion of the fatty acids to methyl esters.

Methanol Recovery from Preparation of Methyl Esters

Following the trans-esterification unreacted-methanol is recovered by passing a stream of air through the agitated volume via inlet and outlets of the vessel.

The methanol laden air is passed through a heat exchanger where the temperature is lowered and the methanol condenses. The methanol is then re-circulated through the volume to remove further methanol. The recovered methanol is suitable for use in the trans-esterification without any further purification.

Washing and Drying

The volume is washed with water by known methods and entrained water removed by passing a stream of air through the agitated volume via inlet and outlets of the vessel.

The moisture laden air is passed through a heat exchanger where the temperature is lowered and the water condenses. The air is then re-circulated through the volume of tallow to remove further water.

Apparatus

The steps of the general method are most advantageously applied to the batch production of biodiesel using the apparatus of FIG. 1.

The apparatus includes a vessel (1) provided with an inlet (2) adapted to receive a flow of air delivered by a gas recirculator (3) into a volume of a source of oil or fat received in the reactor tank (4) of the vessel (1).

The flow of air is used in the method to aerate the volume of a source of oil or fat via an air sparge line (5) located proximal to the base of the volume received in the reactor tank (4). Heating and cooling coils (6) permit heating of the volume to a temperature sufficient to maintain the volume in a liquid form.

As the flow of air is recirculated via the gas recirculator (3) and the outlet (5) entrained water or methanol removed from the volume is condensed by passing the vapour-laden air stream through a heat exchanger (8) to condense the vapour to be collected in a graduated tank (9).

The collected methanol is recovered from the graduated tank (9) via an outlet valve (10). The apparatus therefore provides a closed system for the batch preparation of biodiesel from a source of oil or fat.

The apparatus is fitted with additional inlet and outlet valves (11, 12 and 13) to permit introduction and recovery of the agents and products for each step of the general method. All steps in the general method may be performed using the apparatus with consequential reduction in costs for establishing production facilities.

EXAMPLE

A weighed volume (15580 Kg) of tallow containing approximately 0.1% (w/w) water was delivered to the reactor tank (4) and heated by means of the heating coils (6) to a temperature of 60° C.

The volume of tallow was maintained at this temperature with operation of the gas recirculator (3) for 21 hours. A volume of 8 liters of water collected in the graduated tank (9). The dehydrated tallow was determined to contain approximately 0.04% (w/w) water.

A volume of dehydrated and transesterified tallow containing approximately 3% (w/w) of methanol was aerated for 40 hours by operation of the gas recirculator (3) at a temperature of 60° C. A volume (450 liters) of methanol was collected in the graduated tank (9). The methanol content was determined to be reduced to 0.2% (w/w).

It will be recognized that the method and apparatus are particularly suited for the distributed production of biodiesel as is required in regions of the world lacking the infrastructure to transport the source of oil or fat through a centralised production facility, or the costs associated with this transport preclude the economic production of biodiesel at a centralised production facility.

Although the invention has been described by way of exemplary embodiments it should be appreciated that variations and modifications may be made without departing from the scope of the invention. Furthermore where known equivalents exist to specific features, such equivalents are incorporated as if specifically referred to in this specification.

INDUSTRIAL APPLICABILITY

An economic and convenient method for the preparation of biodiesel from tallow containing a relatively high portion of free fatty acid and entrained water is provided.

REFERENCES

Judd (2002) *Biodiesel from Tallow*, report prepared for the Energy Efficiency and Conservation Authority, November 2002.
Sims (1983) *The Potential for Rapeseed Oil and Tallow Esters as Fuels for Compression Ignition Engines*, Paper No. 83014, 2nd National Conference on Fuels from Crops, Melbourne Australia. SAE Australasia.
Vasudevan & Briggs (2008) *Biodiesel Production—Current State of the Art and Challenges*, J. Ind. Microbiol. Biotechnol., 35, 421-430.

The invention claimed is:

1. A method of generating biodiesel, said method comprising:
aerating a first liquid to remove water from said first liquid and to generate a second liquid, wherein said aerating said first liquid further comprises aerating said first liquid at a temperature in the range of approximately 60 degrees Celsius to approximately 65 degrees Celsius, wherein said first liquid is selected from a group consisting of a liquid comprising a source of oil and a liquid comprising a source of fat; and combining said second liquid with methanol and an alkali catalyst to form a mixture comprising alkyl esters.

2. The method of claim 1, wherein said first liquid comprises tallow.

3. The method of claim 1, wherein said first liquid comprises greater than approximately 0.5% water (w/w), and wherein said first liquid comprises a free fatty acid content in the range of approximately 1% (w/w) to approximately 4% (w/w).

4. The method of claim 1, wherein said combining said second liquid with said methanol and said alkali catalyst further comprises combining said second liquid with said methanol and said alkali catalyst to convert greater than approximately 99% of fatty acids of said second liquid to said alkyl esters.

5. The method of claim 1, wherein said aerating said first liquid further comprises:
   passing air through said first liquid to remove said water from said first liquid and to generate a vapor, wherein said vapor comprises said air and said water; and
   passing said vapor through a heat exchanger to remove said water from said vapor via condensation.

6. The method of claim 1, wherein said combining said second liquid with said methanol and said alkali catalyst further comprises combining said second liquid with said methanol and said alkali catalyst at a temperature in the range of approximately 60 degrees Celsius to approximately 65 degrees Celsius.

7. The method of claim 1 further comprising:
   aerating said mixture to remove a portion of said methanol from said mixture, wherein said aerating said mixture further comprises aerating said mixture at a temperature in the range of approximately 60 degrees Celsius to approximately 65 degrees Celsius.

8. The method of claim 7, wherein said aerating said mixture further comprises:
   passing air through said mixture to remove said portion of said methanol from said mixture and to generate a vapor, wherein said vapor comprises said mixture and said portion of said methanol; and
   passing said vapor through a heat exchanger to remove said portion of said methanol from said vapor via condensation.

9. The method of claim 1 further comprising:
   combining said second liquid with said methanol and a mineral acid catalyst to reduce a free fatty acid content of said second liquid to less than approximately 1.5% (w/w).

10. The method of claim 1 further comprising:
    removing glycerol from said mixture.

11. The method of claim 1, wherein said mixture comprises a ratio of less than one of said second liquid to said methanol.

\* \* \* \* \*